(12) United States Patent
Aguadisch et al.

(10) Patent No.: US 6,379,689 B1
(45) Date of Patent: Apr. 30, 2002

(54) ARTICLE FOR CONTROLLED AND SUBSTANTIALLY UNIFORM RELEASE OF A VOLATILE ORGANIC SUBSTANCE

(75) Inventors: Louis Michel Jacques Aguadisch, Valbonne; Edouard André Henri Bigot, Le Bar-sur-Loup; André Rudolf Louis Colas, Valbonne; Guy Jean-Pierre Delpech, Grasse; Frédéric Fonta, Antibes; Jean Maurice Eugène Mane, Grasse, all of (FR)

(73) Assignees: Etablissements V. Mane Fils, Le Bar-sur-Loup; Dow Corning France, Lyons, both of (FR)

( * ) Notice: Subject to any disclaimer, the term of this patent is extended or adjusted under 35 U.S.C. 154(b) by 0 days.

(21) Appl. No.: 09/589,137

(22) Filed: Jun. 8, 2000

(30) Foreign Application Priority Data

Jun. 18, 1999 (FR) .............................. 99 07761

(51) Int. Cl.$^7$ .............................. A61L 9/01; A01N 25/34
(52) U.S. Cl. .......................... 424/411; 424/401; 512/4; 521/88; 521/154; 523/102; 524/264; 524/266
(58) Field of Search .............................. 512/4; 424/401, 424/411; 521/88, 154; 523/102; 524/264, 266

(56) References Cited

U.S. PATENT DOCUMENTS

| 4,703,070 A | 10/1987 | Locko et al. |
| 5,437,869 A | * 8/1995 | Kelly .......................... 424/411 |

FOREIGN PATENT DOCUMENTS

| FR | 1 601 586 | 8/1970 |
| FR | 2 689 010 | 10/1993 |
| WO | 98/58624 | 12/1998 |

* cited by examiner

Primary Examiner—Morton Foelak
(74) Attorney, Agent, or Firm—Jacobson Holman, PLLC

(57) ABSTRACT

An article for controlled and substantially uniform release of a volatile active organic substance into the surrounding atmosphere includes a silicone elastomer matrix of desired shape in which are dispersed the volatile substance and an effective amount of an agent for compatibilizing the volatile substance and the silicone elastomer of the matrix. The compatibilizer is an organic solvent with a Hildebrandt solubility parameter from 8 $(cal/cm^3)^{1/2}$ to 14 $(cal/cm^3)^{1/2}$ and a vapor pressure from 0.0005 mm to 0.8 mm of mercury (0.06 Pa to 105 Pa) at 20° C.

11 Claims, 1 Drawing Sheet

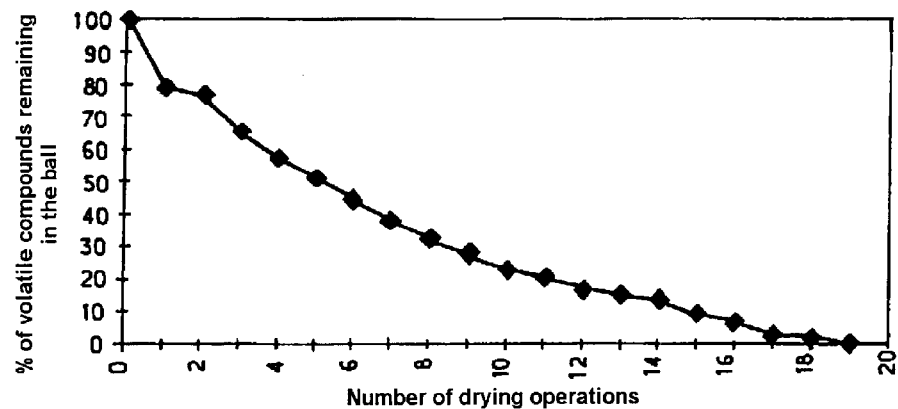
FIG.:1
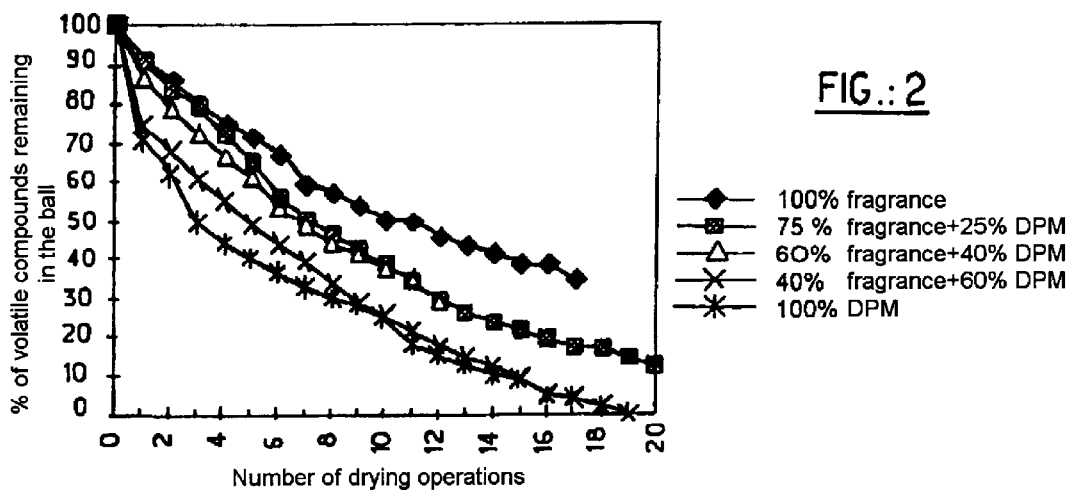
FIG.:2
- ◆ — 100% fragrance
- ▧ — 75 % fragrance+25% DPM
- △ — 60% fragrance+40% DPM
- ✕ — 40% fragrance+60% DPM
- ✳ — 100% DPM
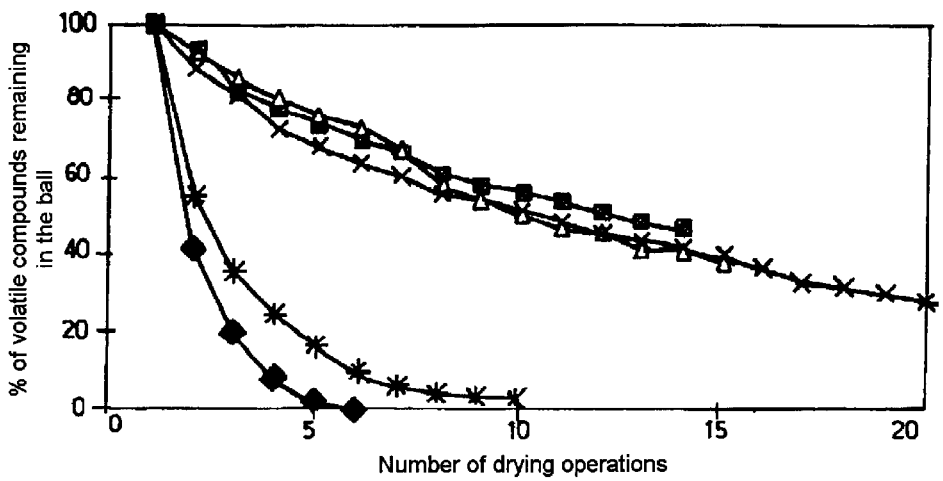
FIG.:3
- ▧ — 75 % fragrance+25% MMB
- △ — 75 % fragrance+25% Emkanol
- ✳ — 75 % fragrance+25% PM
- ◆ — 75 % fragrance+25% DC344
- ✕ — 75 % fragrance+25% DPM

ARTICLE FOR CONTROLLED AND SUBSTANTIALLY UNIFORM RELEASE OF A VOLATILE ORGANIC SUBSTANCE

BACKGROUND OF THE INVENTION

1. Field of the Invention

The invention relates to an article for controlled and substantially uniform release of a volatile organic substance into the surrounding atmosphere. The volatile substance can be in particular a fragrance, an insecticide or an insect repellent.

2. Description of the Prior Art

Silicone elastomers are permeable to gases and liquids. Studies of diffusion of fragrance across a silicone wall are abundant, while studies of diffusion across a silicone matrix are fewer in number. Japanese patent No. 82-40 558 describes a method of manufacturing a silicone elastomer matrix for diffusing fragrance into the atmosphere. The silicone elastomer composition is mixed with the fragrance and, after adding an organometallic salt, curing of the composition is then initiated in a mold. The matrix obtained has a nonlinear diffusion of the fragrance due to an incompatibility between the polymer and the fragrancing composition.

U.S. Pat. No. 4,703,070 shows the importance of incorporating a compatibilizer in order to avoid exudation of the fragrance over time. It describes a method of manufacturing a matrix consisting of a silicone elastomer, a compatibilizer and a fragrance. However, this matrix does not give a linear diffusion of a composition which is constant over time and for temperatures ranging from 15° C. to 60° C.

There is thus a need for an article allowing controlled and substantially uniform release of a volatile organic substance such as a fragrancing composition, an insecticidal composition or an insect-repellent composition, over a broad range of working temperatures.

The invention has for purpose to satisfy this need.

SUMMARY OF THE INVENTION

The invention relates more particularly to an article for controlled and substantially uniform release of a volatile active organic substance into the surrounding atmosphere, the article including a silicone elastomer matrix (a) of desired shape in which are dispersed the volatile substance (b) and an effective amount of an agent (c) for compatibilizing the volatile substance and the silicone elastomer of the matrix, wherein the compatibilizer (c) is an organic solvent with a Hildebrandt solubility parameter from 8 $(cal/cm^3)^{1/2}$ to 14 $(cal/cm^3)^{1/2}$ and a vapor pressure from 0.0005 mm to 0.8 mm of mercury (0.06 Pa to 105 Pa) at 20° C.

According to one specific embodiment the volatile organic substance is a fragrance or a fragrancing composition.

According to another preferred embodiment at least one of the following optional additional constituents is dispersed in the matrix:

an emulsifier (d) in a proportion which is effective in avoiding sweating or exudation of the volatile substance (b) from the matrix (a) during storage of the article, and a silicone fluid (e) in a proportion which is effective in facilitating release of the volatile substance (b) at temperatures from 35° C. to 60° C.

BRIEF DESCRIPTION OF THE FIGURES

FIGS. 1–3 illustrate a comparison of a percent of volatile compounds remaining in the bail for a number of drying operations.

DETAILED DESCRIPTION OF THE INVENTION

As a guide the various constituents (a) to (e) can be used in the following proportions, expressed as percentages by weight relative to the total weight of the constituents (a) to (e):

|  | Broad range | Preferred range |
| --- | --- | --- |
| silicone elastomer (a): | 60–99 | 75–85 |
| volatile active substance (b) + solvent (c): with the condition that the solvent (c)/substance (b) weight ratio is from 1/99 to 99/1 | 1–40 | 15–25 |
| emulsifier (d): | 0–3 | 0.5–2 |
| silicone fluid (e): | 0–15 | 0–10 |

The silicone elastomer (a) can be chosen from the various types of silicone elastomer known in the art. Silicone elastomers which are preferred are those obtained from silicone elastomer compositions which cure at room temperature (known as "RTV" compositions), for example due to the effect of ambient moisture. These RTV silicone elastomer compositions are well known in the art and are commercially available from many suppliers. They are typically packaged in two parts, namely a silicone elastomer base and a crosslinking agent, which are mixed together at the time of use, for example in a mold. Elastomeric compositions which cure due to the effect of heating or radiation are also suitable, as are curable compositions in two or even three reactive parts.

A commercially available silicone elastomer composition which has been found to be suitable consists of the base 3481 and the curing agent DC Silastic 81 sold by Dow Corning Corporation.

The volatile active substance (b) can be a fragrancing substance, an insecticide or an insect repellent, inter alia. The volatile active substance is preferably a fragrancing substance.

The fragrancing substance can be chosen from a large number of odoriferous compounds. Nonlimiting examples of these are the substances belonging to the following families:

aromatic, terpene and/or sesquiterpene hydrocarbons, in particular essential oils containing these molecules and more particularly essential oils of citrus fruit (lemon, orange, grapefruit, bergamot), nutmeg, etc., aromatic alcohols and more particularly benzyl alcohol, phenylethyl alcohol and phenylpropyl alcohol, cyclic or acyclic, saturated or unsaturated, primary, secondary or tertiary nonaromatic alcohols and more particularly linalool, citronellol, geraniol, nerol, dihydromyrcenol, terpineol and fatty alicyclic alcohols whose chain contains from 4 to 10 carbon atoms, aldehydes and more particularly saturated and unsaturated alicyclic fatty aldehydes whose carbon chain contains from 4 to 12 carbon atoms, aromatic aldehydes such as cinnamaldehyde, alpha-amylcinnamaldehyde and alpha-hexylcinnamaldehyde, lilial and phenolic aromatic aldehydes such as vanillin and ethylvanillin, phenols and more particularly aromatic phenols such as eugenol and isoeugenol, as well as methylethers thereof, carboxylic acid esters, in particular the acetic esters of benzyl alcohol, geraniol, citronellol, nerol, terpineol, borneol or linalool, aromatic acid esters such as benzoates and salicylates, as well as cinnamates esterified with alcohols of the aliphatic series containing a chain of 1 to 6 carbon atoms, aromatic phenol acids mainly in their lactone/aromatic form, such as coumarin and dihydrocoumarin, carboxylic alcohol acids in their lactone form, and more particularly the gamma octa-, gamma undeca- and gamma dodeca-lactones and the delta deca-, delta undeca- and delta dodeca-lactones in their saturated or unsaturated form, macrocyclic compounds in which the carbon chain contains from 12 to 16 carbon atoms, aromatic and/or nonaromatic ethers and acetals in their acyclic or cyclic form, and more particularly aldehyde acetals containing a carbon chain of 4 to 10 carbon atoms, as well as substituted furan and substituted or unsubstituted pyran cyclic ethers, heterocyclic compounds containing a nitrogen atom, and more particularly indole derivatives, as well as heterocyclic compounds containing 2 nitrogen atoms, and more particularly those of the pyrazine series, ketones, in particular aromatic ketones such as 4-(p-hydroxyphenyl)-2-butanone and cyclic or acyclic, saturated or unsaturated nonaromatic ketones and more particularly those of the pyrazine series, aromatic or nonaromatic sulfides, disulfides and mercaptans.

The fragrancing substance can consist of a single odoriferous compound or a mixture of such compounds.

Hesperid, floral and fruity fragrances have been found to be particularly suitable.

The solvent (c) is the essential constituent of the article of the invention.

The solvent to be used should have a vapor pressure from 0.0005 mmHg to 0.8 mmHg (0.06 Pa to 105 Pa) at 20° C., preferably from 0.001 mmHg to 0.6 mmHg (0.13 Pa to 79 Pa) at 20° C.

Below 0.0005 mmHg, the solvent is insufficiently volatile and has a tendency to accumulate on the outer surface of the matrix, forming an unappealing greasy film. Above 0.8 mmHg, the solvent is too volatile and the resulting article releases the active substance too quickly.

The solvent (c) should further have a Hildebrandt solubility parameter $\delta$ from 8 $(cal/cm^3)^{1/2}$ to 14 $(cal/cm^3)^{1/2}$, preferably from 10 $(cal/cm^3)^{1/2}$ to 12 $(cal/cm^3)^{1/2}$, in order to ensure satisfactory compatibility between the silicone matrix and the active substance. Suitable compatibility is not obtained below a value of 8 $(cal/cm^3)^{1/2}$ or above a value of 14 $(cal/cm^3)^{1/2}$.

A number of examples of solvents which satisfy the above criteria are given below as nonlimiting illustrations:

| | $\delta$ $(cal/cm^3)^{1/2}$ | Vapor pressure in mmHg |
|---|---|---|
| dipropylene glycol monomethyl ether (1) | 10.35 | 0.0451 |
| diethylene glycol ethyl ether (2) | 10.95 | 0.0693 |
| 3-methyl-3-methoxybutanol (3) | 9.33 | 0.5 |
| diethylene glycol methyl ether | 11.40 | 0.1086 |
| triethylene glycol methyl ether | 10.96 | 0.0037 |
| diethylene glycol n-butyl ether | 10.30 | 0.0120 |
| diethylene glycol hexyl ether | 9.91 | 0.0018 |

-continued

| | $\delta$ $(cal/cm^3)^{1/2}$ | Vapor pressure in mmHg |
|---|---|---|

(1) Dowanol DPM from Dow Chemical Corporation
(2) Emkanol EMK from ICI
(3) abbreviated to MMB hereinbelow The sum of the solvent (c) and the active substance (b) should represent from 1% to 40% of the sum of the constituents (a) to (e), preferably from 15% to 25%. The solvent/volatile active substance weight ratio is not particularly critical and can range from 1/99 to 99/1. This ratio is preferably from 3/7 to 2/8, in particular about 1/3.

A silicone fluid (d) is recommended for use in articles which are intended for use at relatively high temperatures, i.e. from 35° C. to 60° C., since this constituent usually has a moderate volatility at normal ambient temperatures (20° C.). The addition of this optional constituent affords a substantially linear release even when the ambient temperature is high (35–60° C).

Silicone fluids (d) which can be used in particular include dimethicones, cyclomethicones or dimethiconol. The choice of a particular silicone fluid should be made as a function of the application and working temperature of the article. The proportion of the fluid (d) can range from 0% to 15% by weight. The fluids sold by the Dow Corning Corporation under the trade names DC 345 (cyclomethicone), DC 1401 and DC 200 have been found to be suitable.

The optional emulsifier (e) is useful for avoiding the problems of sweating or exudation of the active substance (b) during storage of the article. Emulsifiers (e) which can be used include surfactants of any type, such as Tween® 20 (polysoibate 20), polyethoxylated hydrogenated castor oil (PE6-40), polysorbate 40, polysorbate 80, etc. It suffices for the emulsifier (e) to be capable of maintaining in emulsified form the various starting materials used to prepare the article of the invention up to the curing of the silicone elastomer.

The article of the invention can be manufactured in a simple manner by mixing a silicone elastomer base, the volatile active substance, the solvent and, optionally, the silicone fluid and the emulsifier, with the aid of an energetic stirring device.

The curing agent is then added with stirring and the emulsion obtained is placed under a partial vacuum to degas it. The degassed emulsion is then injected under pressure into a mold in which the silicone elastomer base undergoes cold curing due to the action of the curing agent. All that then remains is to remove the article from the mold and package it in leakproof wrapping. The article of the invention can be molded into any desired shape, for example in the shape of a ball, a cube, a cylinder, a polygonal structure, etc.

In the preferred embodiment in which the active volatile substance is a fragrancing substance, the article of the invention can be used to fragrance a place, as a deodorizer, for example for toilets or cars, as a means for fragrancing laundry in a tumble dryer, etc.

The nonlimiting examples which follow are given for the purpose of illustrating the invention. The general preparation method described above was used in each of the examples.

EXAMPLE 1

An article according to the invention for use in a tumble dryer was prepared from the formulation below:

| Constituents | % by weight |
|---|---|
| silicone elastomer base DC 3481 | 72.5 |
| DC Silastic 81 curing agent | 7.5 |
| fragrance* | 11 |
| Dowanol DPM | 4 |
| DC 345 silicone fluid | 4 |
| Tween 20 (emulsifier) | 1 |

*"Alex" sold by the Etablissements V. Mane Fils company under catalog No. M. 52548 was used as fragrance in this and the following examples.

The article obtained, in the form of a ball 35 mm in diameter, was tested in a tumble dryer with 4 kg of wet laundry at 55° C. for 70 min. The loss of volatile compounds (fragrance+solvent) in each drying operation is given by the difference in mass of the article between two drying operations.

FIG. 1 gives the percentage of volatile compounds remaining in the article as a function of the number of drying operations. It is clearly seen that the diffusion is linear.

EXAMPLE 2

Test Protocol:

A 4 kg load of laundry was washed in a washing machine using a nonfragranced laundry detergent, then submitted to a spin cycle.

The laundry was then placed in a tumble dryer with a silicone ball 35 mm in diameter and weighing about 30 g, having the following formulation:

| Constituents | % by weight |
|---|---|
| silicone elastomer base DC 3481 | 72.50 |
| DC Silastic 81 curing agent | 7.50 |
| fragrance* | 11.25 |
| Dowanol DOM | 3.75 |
| DC 345 silicone fluid | 4.00 |
| Tween 20 (emulsifier) | 1.00 |

In parallel, a similar test was carried out with a commercial product consisting of a piece of fabric impregnated with the same fragrance, which is a "dryer-sheet" product commonly found on the US market. Drying cycle: 50° C. for 70 minutes.

The laundry was then evaluated by a panel of 15 people by comparing the difference in intensity and pleasant nature of the fragrancing after the drying cycle (To) and then 24 hours later ($T_{24}$).

This test was carried out with balls which had undergone 2, 10 and 18 drying cycles, each time in comparison with a new dryer-sheet.

Results Question: Which laundry load had the most intense fragrance?

| | Ball 2nd cycle | "Dryer sheet" | Ball 10th cycle | "Dryer sheet" | Ball 18th cycle | "Dryer sheet" |
|---|---|---|---|---|---|---|
| Intensity To | 86.6% | 13.4% | 80.0% | 20.0% | 60% | 40.0% |
| Intensity $T_{24}$ | 93.3% | 6.7% | 80.0% | 20.0% | 80% | 20.0% |

Question: Which laundry load had the most pleasant fragrance?

| | Ball 2nd cycle | "Dryer sheet" | Ball 10th cycle | "Dryer sheet" | Ball 18th cycle | "Dryer sheet" |
|---|---|---|---|---|---|---|
| Intensity To | 100.0% | 0.0% | 93.3% | 6.7% | 66.6% | 33.4% |
| Intensity $T_{24}$ | 93.3% | 6.7% | 80.0% | 20.0% | 66.6% | 33.4% |

It may be observed that most of the panel members selected the dried with a silicone ball, for both the intensity and the pleasant nature agrance, even after 24 hours.

EXAMPLE 3

This example demonstrates the importance of the solvent (c). The articles were prepared using formulations 2 to 6 similar to formulation 1 of Example 1, except that the relative proportions of solvent and fragrance were varied while keeping the solvent+fragrance sum equal to 15% by weight.

The table below summarizes the compositions of formulations 2 to 6.

| Formulation | DC 3481 | Silastic 81 | Fragrance | Dowanol DPM | DC 345 | Tween 20 |
|---|---|---|---|---|---|---|
| 2 | 72.5 | 7.5 | 15 | 0 | 4 | 1 |
| 3 | 72.5 | 7.5 | 11.25 | 3.75 | 4 | 1 |
| 4 | 72.5 | 7.5 | 9 | 6 | 4 | 1 |
| 5 | 72.5 | 7.5 | 6 | 9 | 4 | 1 |
| 6 | 72.5 | 7.5 | 0 | 15 | 4 | 1 |

The articles, in the form of a ball 35 mm in diameter, were tested in a tumble dryer with 4 kg of wet laundry at 60° C. and for 70 min.

FIG. 2 shows the percentage of volatile compounds (fragrance+solvent) remaining in the articles as a function of the number of drying operations. It is seen that the release of the volatile compounds was proportionately faster and more extensive the larger the amount of solvent.

EXAMPLE 4

In this example, five different solvents were tested, three in accordance with the invention and two outside the scope of the invention, to prepare five formulations 7 to 11 having the composition in terms of % by weight indicated in the table below.

The two solvents not satisfying the criteria of the present invention were:

propylene glycol methyl ether (sold under the trade name Dowanol PM by Dow Chemical Corporation), with a Hildebrandt solubility parameter of 11.1 $(cal/cm^3)^{1/2}$ and a vapor pressure of 8.74 mmHg at 20° C., a cyclomethicone (sold under the trade name DC 344 by Dow Corning) with a Hildebrandt solubility parameter of 5.98 $(cal/cm^3)^{1/2}$ and a vapor pressure of 1.1649 mmHg at 20° C.

| Formulation | DC 3481 | Silastic 81 | Fragrance | Solvent | | | | |
|---|---|---|---|---|---|---|---|---|
| | | | | MM B | Emkanol EMK | Dowanol DPM | Dowanol PM** | DC34 4** |
| 7 | 72.5 | 7.5 | 15 | 5 | — | — | — | — |
| 8 | 72.5 | 7.5 | 15 | — | 5 | — | — | — |
| 9 | 72.5 | 7.5 | 15 | — | — | 5 | — | — |
| 10 | 72.5 | 7.5 | 15 | — | — | — | 5 | — |
| 11 | 72.5 | 7.5 | 15 | — | — | — | — | 5 |

**not according to the invention; given for comparison.

These formulations were used to prepare ball-shaped articles 35 mm in diameter which were tested in a tumble dryer as in the previous examples.

FIG. 3 shows the percentage of volatile compounds (fragrance+solvent) remaining in the articles as a function of the number of drying operations. It is seen that the three solvents in accordance with the invention had comparable behaviors, quite superior to the two comparative solvents which were not in accordance with the invention.

It goes without saying that the embodiments described are merely examples and that they may be modified, in particular by replacement with technical equivalents, without thereby departing from the scope of the invention.

What is claimed is:

1. An article for controlled and substantially uniform release of a volatile active organic substance into the surrounding atmosphere, said article including a silicone elastomer matrix (a) of desired shape in which are dispersed said volatile substance (b) and an effective amount of an agent (c) for compatibilizing said volatile substance and said silicone elastomer of said matrix, wherein said compatibilizer (c) is an organic solvent with a Hildebrandt solubility parameter from 8 $(cal/cm^3)^{1/2}$ to 14 $(cal/cm^3)^{1/2}$ and a vapor pressure of from 0.0005 mm to 0.8 mm of mercury (0.06 Pa to 105 Pa) at 20° C.

2. The article claimed in claim 1 wherein said organic solvent has a vapor pressure from 0.001 mmHg to 0.6 mmHg (0.13 Pa to 79 Pa) at 20° C.

3. The article claimed in claim 1 wherein said volatile active substance is a fragrance, a fragrancing composition, an insecticide or an insect repellent.

4. The article claimed in claim 1 wherein said volatile active substance is a fragrance or fragrancing composition.

5. The article claimed in claim 1 wherein at least one of the following optional additional constituents is dispersed in said matrix:
   an emulsifier (d) in a proportion which is effective in avoiding sweating or exudation of said volatile substance (b) from said matrix (a) during storage of said article, and
   a silicone fluid (e) in a proportion which is effective in facilitating release of said volatile substance (b) at temperatures from 35° C. and 60° C.

6. The article claimed in claim 1 wherein the constituents (a) to (e) are used in the following proportions in percentages by weight relative to the total weight of said constituents (a) to (e):
   from 60% to 99% of said silicone elastomer (a)
   from 1% to 40% in total of said volatile active substance (b) and of said solvent (c)
   from 0% to 5% of said emulsifier (d), and
   from 0% to 15% of said silicone fluid (e); with the condition that the weight ratio of said solvent (c) to said volatile substance (b) is from 1/99 to 99/1.

7. The article claimed in claim 6 wherein said weight ratio of said solvent (c) to said volatile substance (b) is from 3/7 to 2/8.

8. The article claimed in claim 7 wherein said weight ratio of said solvent (c) to said volatile substance (b) is about 1/3.

9. The article claimed in claim 1 wherein said solvent (c) has a Hildebrandt solubility parameter from 10 $(cal/cm^3)^{1/2}$ to 12 $(cal/cm^3)^{1/2}$.

10. The article claimed in claim 6 wherein said silicone elastomer (a) represents from 75% to 85%, and the total of said volatile active substance (b) and said solvent (c) represents from 15% to 25%.

11. The article claimed in claim 1 wherein said solvent is dipropylene glycol monomethyl ether.

* * * * *